United States Patent [19]

Juhasz et al.

[11] Patent Number: 4,715,857
[45] Date of Patent: Dec. 29, 1987

[54] WOUND DRESSINGS

[75] Inventors: Laszlo Juhasz, London; Angus I. McLeod, Bucks, both of England

[73] Assignee: Charcoal Cloth Ltd., Berkshire, England

[21] Appl. No.: 882,915
[22] PCT Filed: Apr. 18, 1986
[86] PCT No.: PCT/GB86/00217
§ 371 Date: Nov. 12, 1986
§ 102(e) Date: Nov. 12, 1986
[87] PCT Pub. No.: WO86/05970
PCT Pub. Date: Oct. 23, 1986

[30] Foreign Application Priority Data

Apr. 18, 1985 [GB] United Kingdom ............... 8509977

[51] Int. Cl.⁴ .................................. A61F 13/16
[52] U.S. Cl. .................................. 604/359; 128/156
[58] Field of Search ............ 604/359, 358, 367, 374, 604/375, 376, 377, 378; 128/155, 156

[56] References Cited

U.S. PATENT DOCUMENTS 2,690,415  9/1954  Shuler .
3,299,890  1/1967  Parker .
3,340,875  9/1967  Dudley et al. .
3,903,882  9/1975  Augurt ........................... 128/155
3,939,838  2/1976  Fujinami et al. .
4,088,132  5/1978  Wood et al. .
4,547,195  10/1985  Jackson .

FOREIGN PATENT DOCUMENTS 0053936  6/1982  European Pat. Off. .
0099890  7/1983  European Pat. Off. .
2380688  9/1978  France .
 386067  7/1977  United Kingdom .
1301101  7/1981  United Kingdom .
2127389  4/1984  United Kingdom .

Primary Examiner—John D. Yasko
Attorney, Agent, or Firm—Jeffers, Hoffman & Niewyk

[57] ABSTRACT

A wound dressing which comprises, in order, (1) a first layer of a permeable material;
(2) a layer of a semi-permeable, adhesive material;
(3) a charcoal cloth or felt; and
(4) a second layer of a permeable material;

in which the three said layers are substantially co-extensive and surround the charcoal cloth or felt, whereby the first layer of permeable material is bound to the cloth or felt and, around the cloth or felt, to the second layer of permeable material.

18 Claims, 1 Drawing Figure

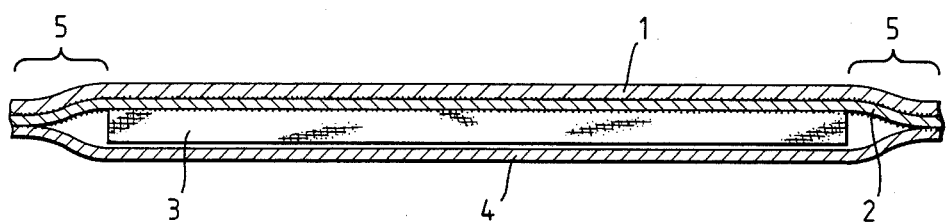

WOUND DRESSINGS

This application is the U.S. National filing of PCT application Ser. No. PCT/GB86/00217, which is a continuation-in-part of U.S. application Ser. No. 733,570, filed May 13, 1985, now abandoned.

FIELD OF THE INVENTION

The present invention relates to anti-bacterial wound dressings. In particular, it relates to integral dressings which can be used to cover contaminated and discharging malodorous wounds, and assist in their treatment. More specifically, it relates to wound dressings comprising activated carbon.

BACKGROUND OF THE INVENTION

The utility of carbonized fabric in surgical dressings has been appreciated for over 50 years. British Patent Specification No. 386,067 disclosed surgical dressings comprising woven or entangled carbonized fibers. Such dressings are also disclosed as supports for therapeutic or antiseptic materials and it is stated that "the dressings will hold in considerable quantities iodine, formol, lime, oxygen, bacillary toxins, and the like". THe use of, say, iodine, in such dressings appears to be a consequence of the adsorptive characteristics of charcoal cloths.

British Patent Specification No. 1,301,101 discloses a particularly useful, and commercially used, process for preparing activated carbon products in fibrous form. Rayon, for example, is impregnated with a solution of inorganic halides and then activated in a controlled heating step.

Activated carbon cloth or felts of the type produced by the process described in British Patent Specification No. 1,301,101 adsorb both organic materials and bacterial. Surgical dressings using activated charcoal impregnated with anti-bacterial agent placed within a permeable teabag-like material are disclosed and illustrated in European Patent Publication No. 53,936, published June 16, 1982; in that case the adsorptive sites of the activated charcoal are no more than 20% saturated with an anti-microbial agent, preferably iodine.

The disadvantage of a dressing of this type is that the agent, incorporated in the dressing, inherently limits the bacteria-adsorbing characteristics of the charcoal and could adversely affect wound healing. The charcoal cloth can easily fragment, and carbon particles can find their way into the wound.

European Patent Publication No. 99,758, published Feb. 1, 1984, discloses a three-layered composite (but not integral) wound dressing comprising a semi-permeable membrane, a permeable supporting and reinforcing layer, and a non-stick, self-sealing biodegradable tissue interface. The permeable layer may be an activated carbon cloth.

British Patent Publication No. 2,127,389A, published Apr. 11, 1984, discloses a surgical dressing comprising activated charcoal cloth or felt which has been produced so that it contains elemental silver distributed throughout. Such a product is at least bacteriostatic, but may not "fix" bacteria or facilitate wound healing.

OBJECT OF THE INVENTION

It is an object of the invention to provide an antibacterial wound dressing which has an integrated structure and assists wound healing. In other words, the wound dressing should provide a barrier against bacterial contamination and mechanical injury, and also provide controlled water vapor transmission and controlled heat loss.

SUMMARY OF THE INVENTION

An antibacterial wound dressing according to the present invention comprises four strata which are, in order, (1) a first layer of a permeable material;
(2) a layer of a semi-permeable, adhesive material;
(3) a charcoal cloth or felt; and
(4) a non-adherent wound-facing layer of a permeable material;

in which the three said layers are substantially co-extensive and surround the charcoal cloth or felt.

BRIEF DESCRIPTION OF THE DRAWING

The accompanying drawing is an enlarged cross-sectional side view (without reference to true relative thicknesses) of a wound dressing which is an illustrative embodiment of the present invention.

DETAILED DESCRIPTION OF THE INVENTION

The integral nature of the dressing according to the present invention is a consequence of the double-sided adhesive properties of the semi-permeable material. The charcoal cloth or felt is thus bound together, via the semi-permeable material, over one entire surface to the first layer of permeable material. The tow layers of permeable material are thus bound together, via the semi-permeable material, in an area which borders the cloth or felt. The only area of non-adherence is over the adjacent faces of the cloth or felt and the second, wound-facing permeable material, making this surface of the dressing entirely suitable as that intended to contact the wound, in use. A wound dressing of the invention may carry a marker indicating the opposite side to the wound-facing surface.

The drawing shows a first layer of permeable material 1, a layer of semi-permeable double-sided adhesive material 2, an activated charcoal fabric 3 and a second layer of permeable material 4. The permeable layers 1 and 4 are bonded by the semi-permeable adhesive layer at the border area 5 of the product, i.e. around the fabric 3. It is intended that layer 4 should come into contact with a wound. Bacteria in the atmosphere which come into contact with layers 1 and 2 are prevented from passing to the wound.

The "enveloping" layers of the permeable material may be of different or, preferably, the same material. Examples of suitable materials are natural or synthetic rubber, nylon, polyester, polyurethane and rayon acetate, and other suitable synthetic polymers. The material should be in the form of a fabric or film having a pore size of, say, 50 to 500 $\mu$m, but preferably 150 to 200 $\mu$m.

The cloth or felt may be of the activated type, e.g. prepared as described in British patent Specification No. 1,301,101. It is preferably a woven fabric of activated carbon, but any activated charcoal fabric, made from, e.g. paper or other cellulosic material may be used.

Semi-permeable adhesive materials are known, e.g. in the form of a "transfer tape". A double-sided transfer tape, with a pore size of less than 50 $\mu$m, derived from rayon acetate and polyurethane, is available from the 3M Company Ltd. Preferably, the material has a pore size of less than 20 μm, and provides water vapor transmission of 200 to 2000 g/m²/24h.

The size of a wound dressing of the invention may be defined as desired. For example, the cloth or felt may be about 140×90 mm and the three said layers each about 150×100 mm in area, so that the border around the cloth or felt is about 10 mm wide. An alternative embodiment comprises a relatively wide border on two sides of the cloth or felt, so that the product has more the appearance of a strip. Again, the dressing can be formulated as a bandage. For use, the dressing may be provided together with a release liner.

A product of the invention has anti-bacterial characteristics in that it absorbs bacteria, reduces bacterial growth (by limiting oxygen availability), and provides a bacterial barrier, thereby minimizing external and cross-contamination. The dressing has wound-healing characteristics because it controls water vapor transmission, thereby maintaining a humid environment which allows the natural wound-healing processes to function.

The wound-facing permeable layer is essentially non-adherent to the wound. The dressing can be adsorbent with respect to exudate, and eliminate offensive odors.

A primary advantage of a wound dressing of the invention is that it is anti-bacterial and assists wound management. It can be used for the treatment of infected and discharging, ulcerated and permanent, cancerous and malodorous, and contaminated and burn wounds. Its structure is integrated and can be non-fraying. In particular, the charcoal cloth or felt is bound over its area; fraying, which occurs if such a material is merely loosely held, with potential shedding of carbon fabric particles into a wound, is prevented.

Three examples of dressings of the invention have been prepared. Their respective sizes are 100 mm×150 mm, 150 mm×190 mm and 190 mm×280 mm. Their respective dressing surface areas are 158 cm², 285 cm² and 532 cm². Their respective apparent surface areas are 1600 m², 2160 m² and 6720 m². Their respective weights are 3.8 g, 7 g and 14.4 g. Their respective fluid contents on saturation with water are 12.5 ml, 25 ml and 50 ml. In each case, the fluid absorption on saturation is 375%, the fluid absorption rate is 100 mg/sec, the carbon particle release with respect to activated charcoal cloth is 0.01%, and the bacterial absorption (reduction in log.) is 3–5.

The invention has been illustrated and described by way of reference with respect to preferred embodiments, but it is to be understood that integers of the invention may be changed or modified within the scope of the invention, as defined by the appended claims. The four defined strata are essential, but not exclusive, features of the invention.

We claim:

1. An anti-bacterial wound dressing comprising:
a first layer of permeable material,
a layer of semi-permeable adhesive material,
a layer of charcoal fabric,
a second layer of permeable material,
said first and second permeable layers and said semi-permeable layer being coextensive and surrounding said charcoal fabric, said first permeable layer being bound to said charcoal fabric layer and to said second permeable layer adjacent the periphery of said charcoal fabric layer.

2. A wound dressing according to claim 1 wherein the semi-permeable material has a pore size of less than 20 μm.

3. The wound dressing of claim 1 wherein said layer of charcoal fabric is comprised of an activated charcoal fabric.

4. The wound dressing of claim 3 wherein the semi-permeable material has a pore size less than 20 μm.

5. A multi-layered antibacterial wound dressing for application to a wound wherein each layer includes opposite surfaces wherein one surface faces away from the wound and the other surface faces toward the wound, the dressing comprising the following layers:
a first permeable layer,
a semi-permeable layer having adhesive on both surfaces thereof, said first permeable layer being adhered over its entire other surface to said semi-permeable layer over its entire one surface,
a charcoal fabric layer adhered over its entire one surface to said semi-permeable layer, and
a second permeable layer having the one surface thereof adjacent to the other surface of said charcoal fabric layer, said second permeable layer adhered adjacent the periphery of its one surface to said semi-permeable layer so as to envelope said charcoal fabric layer.

6. The wound dressing of claim 5 wherein said first permeable layer is made from a material in the form of a fabric having a pore size between about 50 μm and about 500 μm.

7. The wound dressing of claim 5 wherein said first permeable layer is made from a material in the form of a fabric having a pore size of between about 150 μm and about 200 μm.

8. The wound dressing of claim 5 wherein said semi-permeable layer is made from a material in the form of a tape having a pore size of less than 20 μm.

9. The wound dressing of claim 5 wherein the other surface of said second permeable layer contacts the wound upon application of the dressing.

10. The wound dressing of claim 5 wherein said charcoal fabric layer is adhered only to said semi-permeable layer.

11. An antibacterial wound dressing comprising:
an envelope of permeable material including a pair of oppositely disposed top and bottom members,
charcoal means, contained within the envelope, for facilitating the antibacterial activity of the dressing, and
semi-permeable adhesive means for adhering said charcoal means to said to member and adhering the top and bottom members together adjacent the periphery of the charcoal means.

12. The wound dressing of claim 11 wherein said top and bottom members are made of the same material.

13. The wound dressing of claim 11 wherein said charcoal means comprises a layer of activated charcoal fabric.

14. The wound dressing of claim 11 wherein said semi-permeable means comprises a layer of material having adhesive on both sides thereof.

15. The wound dressing of claim 14 wherein said semi-permeable layer is made from a material in the form of a tape having a pore size less than 20 μm.

16. The wound dressing of claim 15 wherein said semi-permeable layer is made from a material in the form of a tape having a vapor transmission rate between about 200 grams per square meter per 24 hours and about 2000 grams per square meter per 24 hours.

17. The wound dressing of claim 1 wherein said semi-permeable layer is made from a material in the form of a tape having a vapor transmission rate between about 200 grams per square meter per 24 hours and about 2000 grams per square meter per 24 hours.

18. The wound dressing of claim 5 wherein said semipermeable layer is made from a material in the form of a tape having a vapor transmission rate between about 200 grams per square meter per 24 hours and about 2000 grams per square meter per 24 hours.

* * * * *